United States Patent
Strobl (10) Patent No.: US 10,537,394 B2
(45) Date of Patent: Jan. 21, 2020

(54) HOT DEVICE INDICATION OF VIDEO DISPLAY

(71) Applicant: Ethicon Endo-Surgery, Inc., Cincinnati, OH (US)

(72) Inventor: Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 351 days.

(21) Appl. No.: 15/383,068

(22) Filed: Dec. 19, 2016

(65) Prior Publication Data

US 2018/0168734 A1 Jun. 21, 2018

(51) Int. Cl.
*A61B 34/20* (2016.01)
*A61B 5/06* (2006.01)
(Continued)

(52) U.S. Cl.
CPC ............ *A61B 34/20* (2016.02); *A61B 5/0075* (2013.01); *A61B 5/064* (2013.01); *A61B 5/065* (2013.01);
(Continued)

(58) Field of Classification Search
CPC ......... A61B 34/20; A61B 34/30; A61B 34/35; A61B 34/74; A61B 34/76; A61B 5/0075;
(Continued)

(56) References Cited

U.S. PATENT DOCUMENTS 8,027,710 B1 9/2011 Dannan
8,114,345 B2 2/2012 Dlugos, Jr. et al.
(Continued)

FOREIGN PATENT DOCUMENTS

WO WO-2010102197 A2 9/2010
WO WO-2014151621 A1 9/2014
WO WO-2014168987 A1 10/2014

OTHER PUBLICATIONS

International Search Report and Written Opinion for International App. No. PCT/US2017/064423 dated Mar. 23, 2018 (16 pages).

*Primary Examiner* — Paula J Stice
(74) *Attorney, Agent, or Firm* — Mintz Levin Cohn Ferris Glovsky and Popeo, P.C.

(57) ABSTRACT

A surgical system includes a first detector that includes a first array of pixels configured to detect light reflected by a surgical instrument and generate a first signal comprising a first dataset representative of a visible image of the surgical instrument. The surgical system also includes a second detector, comprising a second array of pixels configured to detect infrared radiation produced by the surgical instrument during a procedure using the surgical instrument and generate a second signal comprising a second dataset representative of an infrared image of the surgical instrument. The surgical system further includes a processor configured to receive the first and second signals, identify from the first dataset data representative of the surgical instrument, and identify from the second dataset data representative of one or more regions of the surgical instrument above a predetermined threshold temperature. The processor is also configured to generate a modified image of the surgical instrument based on data identified from the first and second dataset. The modified image includes visible indicia in the one or more region of the surgical instrument at or above the predetermined temperature.

12 Claims, 8 Drawing Sheets

(51) Int. Cl.
*A61B 5/00* (2006.01)
*A61B 18/14* (2006.01)
*A61N 7/02* (2006.01)
*A61B 17/00* (2006.01)
*A61B 34/35* (2016.01)
*A61B 34/00* (2016.01)
*A61B 90/00* (2016.01)

(52) U.S. Cl.
CPC .... *A61B 17/00234* (2013.01); *A61B 18/1445* (2013.01); *A61B 34/35* (2016.02); *A61B 34/74* (2016.02); *A61B 34/76* (2016.02); *A61B 90/39* (2016.02); *A61N 7/02* (2013.01); *A61B 2034/2051* (2016.02); *A61B 2034/2057* (2016.02); *A61B 2034/2065* (2016.02); *A61B 2034/741* (2016.02); *A61B 2034/742* (2016.02); *A61B 2034/743* (2016.02); *A61B 2034/744* (2016.02); *A61B 2090/3975* (2016.02)

(58) Field of Classification Search
CPC .............. A61B 17/00234; A61B 18/12; A61B 18/1445; A61B 2034/2057; A61B 2034/2065; A61B 2018/00791; A61B 2018/00982; G01J 5/0803
See application file for complete search history.

(56) References Cited

U.S. PATENT DOCUMENTS

| | | |
|---|---|---|
| 2002/0120188 A1 | 8/2002 | Brock et al. |
| 2002/0188293 A1 | 12/2002 | Manzo |
| 2016/0000514 A1 | 1/2016 | Ellman |

HOT DEVICE INDICATION OF VIDEO DISPLAY

FIELD

Methods and devices are provided for minimally invasive surgery, and in particular for providing real-time information regarding the status of a surgical instrument.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of minimally invasive surgery, there remains a need for improved methods, systems, and devices for real-time monitoring of the temperature of surgical instruments in the abdominal cavity.

SUMMARY

Methods, devices, and systems are provided for displaying electrical pathways in end effectors of surgical tools. In one aspect, a surgical tool is provided that includes an elongate shaft and an end effector at a distal end thereof. The end effector has one or more electrodes, at least one of which is configured to have energy pass therethrough. The system is configured to display the status of the electrodes of the end effector (e.g., a relative temperature indication) during a surgical procedure.

In one embodiment, a surgical system includes a first detector that includes a first array of pixels configured to detect visible light reflected by a surgical instrument and generate a first signal comprising a first dataset representative of a visible image of the surgical instrument. The surgical system also includes a second detector, comprising a second array of pixels configured to detect infrared radiation produced by the surgical instrument during a procedure using the surgical instrument and generate a second signal comprising a second dataset representative of an infrared image of the surgical instrument. The surgical system further includes a processor configured to receive the first and second signals, identify from the first dataset data representative of the surgical instrument, and identify from the second dataset data representative of one or more regions of the surgical instrument above a predetermined threshold temperature. The processor is also configured to generate a modified image of the surgical instrument based on data identified from the first and second dataset. The modified image includes visible indicia in the one or more regions of the surgical instrument at or above the predetermined temperature.

The surgical system can vary in a number of ways. The surgical system can include an optical element configured to direct the visible light reflected by the surgical instrument to the first detector and the infrared radiation produced by the surgical instrument to the second detector. The optical element can, for example, be a prism system. The surgical system can include a lens to direct the visible light reflected by the surgical instrument and the infrared radiation produced by the surgical instrument to the optical element.

In one embodiment, the processor identifies data representative of the surgical instrument based on position of the first detector with respect to the surgical instrument and information representative of one or more surgical instruments stored in a database. In another embodiment, the processor determines orientation of the surgical instrument based on the identified data representative of the surgical instrument and a database of one or more surgical instruments stored in memory.

In one embodiment, the surgical instrument includes one or more markers, each of the one or more markers configured to reflect a predetermined frequency of light. In another embodiment, the processor identifies from the first dataset data representative of the surgical instrument through an image recognition algorithm based on location of the one or more markers.

In one embodiment, the processor determines orientation of the surgical instrument based on the identified data representative of the surgical instrument. In another embodiment the processor identifies from the second dataset data representative of one or more regions of the surgical instrument above the predetermined threshold temperature based on the frequency of the infrared radiation produced by the one or more regions of the surgical instrument. For example, the predetermined threshold temperature is about 50° C.

In one embodiment, the frequency of the infrared radiation is at or above a threshold frequency. The threshold frequency and the threshold temperature are related by one or more emissivity parameters associated with the surgical instrument. In another embodiment, the modified image is generated based on position of the first detector with respect to the second detector.

In one embodiment, the surgical instrument includes an energy delivering end effector configured to deliver at least one of ultrasonic energy and radio frequency energy to a tissue. In another embodiment, the surgical system includes a display device to display the modified image.

In one embodiment, the surgical system is a robotic surgical system and the robotic surgical system includes at least one robotic arm configured to hold and manipulate the surgical instrument. In another embodiment, the visible indicia include pixels of a distinct color in the modified image that represent a temperature value at or above the predetermined threshold temperature. For example, the color is red.

In one embodiment, a robotic surgical system includes a robotic arm, a tool assembly removably coupled to the robotic arm. The tool assembly includes a shaft extending distally from a housing and an end effector coupled to a distal end of the shaft, the end effector being configured to deliver energy to tissue for the treatment thereof. The robotic surgical system also includes a camera system configured to capture visible light reflected by at least one of the end effector and the shaft and capture infrared light produced by at least one of the end effector and the shaft. The robotic surgical system further includes a processor configured to receive signals representative of the visible and the infrared light and to identify one or more regions of the end effector and the shaft having a temperature in excess of a predetermined threshold temperature.

The surgical robotic system can vary in a number of ways. In another embodiment, the robotic surgical system includes a display device configured to display a modified image of the end effector and the shaft such that the modified image indicates the one or more regions having a temperature at or above the predetermined threshold temperature. In one configuration, the one or more regions are represented by a distinct color.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The systems, devices, and methods disclosed herein can be implemented using a robotic surgical system. WIPO Patent Publication No. WO 2014/151621 filed on Mar. 13, 2014 and entitled "Hyperdexterous Surgical System" is incorporated by reference.

In general, a surgical system is described that allows a user (e.g., a surgeon) to monitor and display the status of a surgical instrument in real-time. In particular, the monitored and displayed status can relate to temperature. Some surgical instruments treat tissue using an ultrasonic energy source and/or a radio frequency energy source into heat energy. For an ultrasonic device, it is the friction between the tissue and the oscillating blade that generates the heat that achieves the desired sealing/cutting effect. For an RF device, heat is generated as energy is passed through the tissue. In the course of treating tissue heat is transferred from the tissue to the jaws of the device. Regardless of whether ultrasonic or RF devices are used, the heating of the instrument is generally undesirable because after completing a seal the surgeon may sometimes use the instrument as a type of grasper to manipulate tissue. If the jaws are still hot from the last tissue treatment, tissue may be inadvertently damaged while the jaws are used to manipulate tissue or otherwise contact tissue. It is thus useful for a surgeon to understand at any given time the relative temperature of the components of a surgical instrument that will be used to contact tissue. In particular, it is important for the surgeon to understand whether the instrument is too hot and what parts of the instrument are above or below a desired temperature. If the surgical instrument achieves or exceeds a desired temperature, i.e., the temperature of the portion of the surgical instrument achieves or exceeds a threshold value, the tissue that is contacted with the surgical instrument (for treatment or otherwise) can be damaged.

During a minimally invasive procedure, or any surgical procedure in which the surgical instrument is outside of the surgeon's natural field of view, an image of the surgical environment as well as relevant portions of the surgical instrument is typically generated and displayed to the surgeon, such as on a video monitor. Such an image is typically displayed in real-time. In aspects of the system described herein, the image of the surgical instrument is modified to display information regarding its status. In one embodiment, the status is the temperature and/or temperature range of relevant portions of the surgical instrument that will be in contact with the tissue. The status (e.g., temperature) information can be displayed at all times, or only when the temperature exceeds a threshold temperature (e.g., 50° C.). The temperature information can displayed as a value and/or by an indication of value. In one example, portions of the surgical instrument that exceed the threshold temperature can be displayed by highlighting in a certain color (e.g., red), or by using other indicators.

The temperature distribution of the surgical instrument can be obtained using thermal imaging techniques in which the temperature of a surgical instrument can be determined by capturing the infrared radiation emitted by the object. In particular, an infrared camera can be positioned so as to image a surgical site (e.g., one or more of target tissues, tissues surrounding the target tissue, surgical instrument, etc.). The infrared camera captures radiation and sends this information to a processor. The processor also receives information related to the reflected-light image of the surgical site from the visible-light camera. The processor generates a modified image by identifying the surgical instrument from the reflected-light image, and superimposing on the image of the surgical instrument a visual representation of the infrared radiation. Thus, the image displayed to the surgeon in real time will indicate portions of the surgical instrument that exceed a threshold value. For example, in one embodiment, portions of the surgical instrument above a predetermined threshold temperature (e.g., 50° C.) can be highlighted in a predetermined color (e.g., red) or otherwise indicated. In another embodiment, a range of temperatures can be associated with a spectrum of colors or symbols, and regions of the surgical instrument can be highlighted by a color or a symbol that corresponds to the associated temperature. Similarly, the modified image can display an image of the surgical instrument without any status (e.g., temperature) indicia when the temperature is below a predetermined value. Because the modified image includes real-time temperature distribution information of the surgical instrument, the surgeon can take appropriate steps to minimize damage of abdominal cavity due to excessive heating of the surgical instrument.

Figure 1:
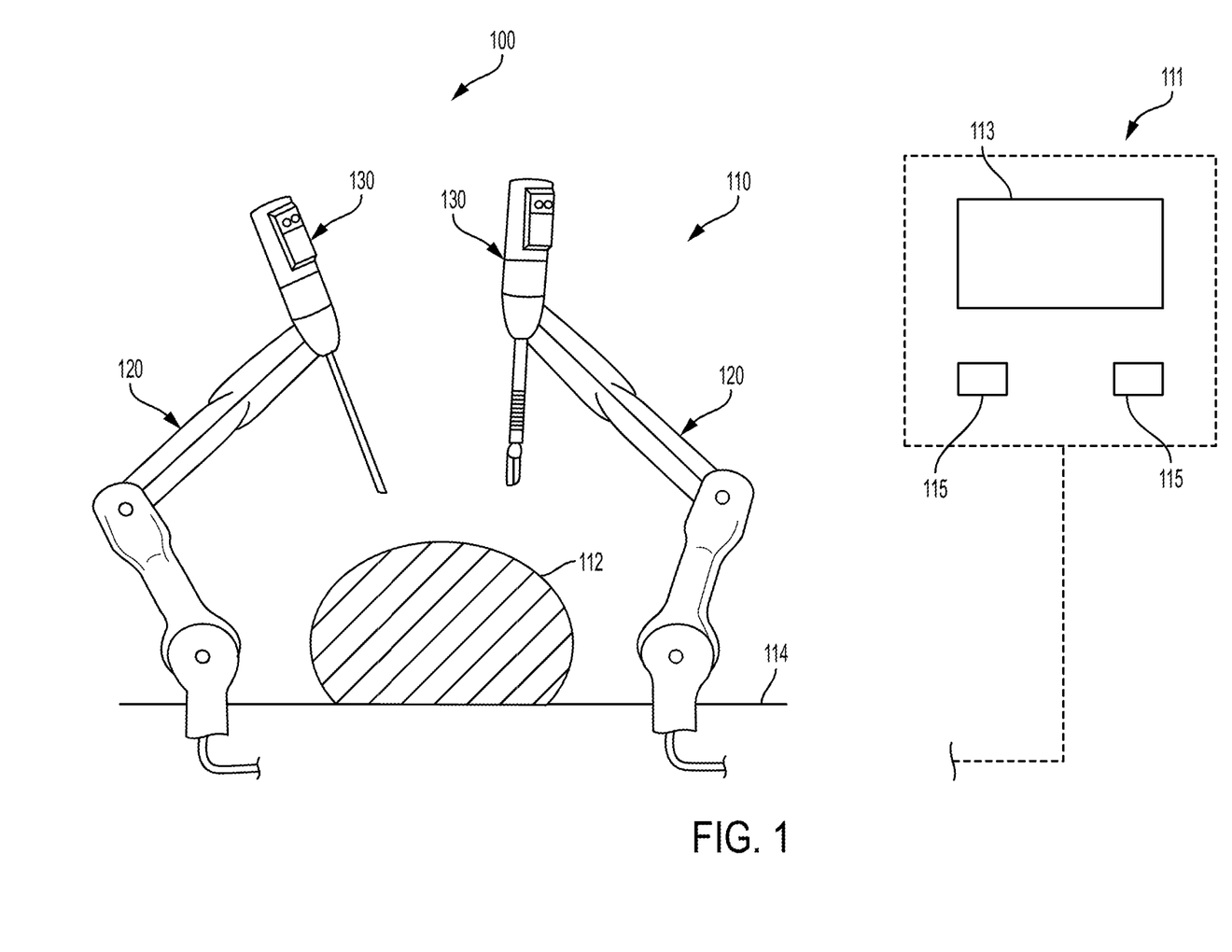
FIG. 1 illustrates a perspective view of an embodiment of a surgical robotic system that includes a patient-side portion and a user-side portion.

FIG. 1 is a perspective view of one embodiment of a surgical robotic system 100 that can be used in telesurgery. The system 100 includes a patient-side portion 110 that is positioned adjacent to a patient 112, and a user-side portion 111 that is located a distance from the patient, either in the same room and/or in a remote location. The patient-side portion 110 generally includes one or more robotic arms 120 and one or more tool assemblies 130 that are configured to releasably couple to a robotic arm 120. The user-side portion 111 generally includes a vision system 113 for viewing the patient 112 and/or surgical site, and a control system 115 for controlling the movement of the robotic arms 120 and each tool assembly 130 during a surgical procedure.

The control system 115 can have a variety of configurations and it can be located adjacent to the patient. e.g., in the operating room, remote from the patient, e.g., in a separate control room, or it can be distributed at two or more locations. As an example of a dedicated system, a dedicated system control console can be located in the operating room, and a separate console can be located at a remote location. The control system 115 can include components that enable a user to view a surgical site of a patient 112 being operated on by the patient-side portion 110 and/or to control one or more parts of the patient-side portion 110 (e.g., to perform a surgical procedure at the surgical site 112). In some embodiments, the control system 115 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 120 and tool assemblies 130.

The patient-side portion can also have a variety of configurations. As depicted in FIG. 1, the patient-side portion 110 can couple to an operating table 114. However, in other embodiments, the patient-side portion 110 can be mounted to a wall, to the ceiling, to the floor, or to other operating room equipment. Further, while the patient-side portion 110 is shown as including two robotic arms 120, more or fewer robotic arms 120 can be included. Furthermore, the patient-side portion 110 can include separate robotic arms 120 mounted in various positions, such as relative to the operating table 114. Alternatively, the patient-side portion 110 can include a single assembly that includes one or more robotic arms 120 extending therefrom.

Figure 2:
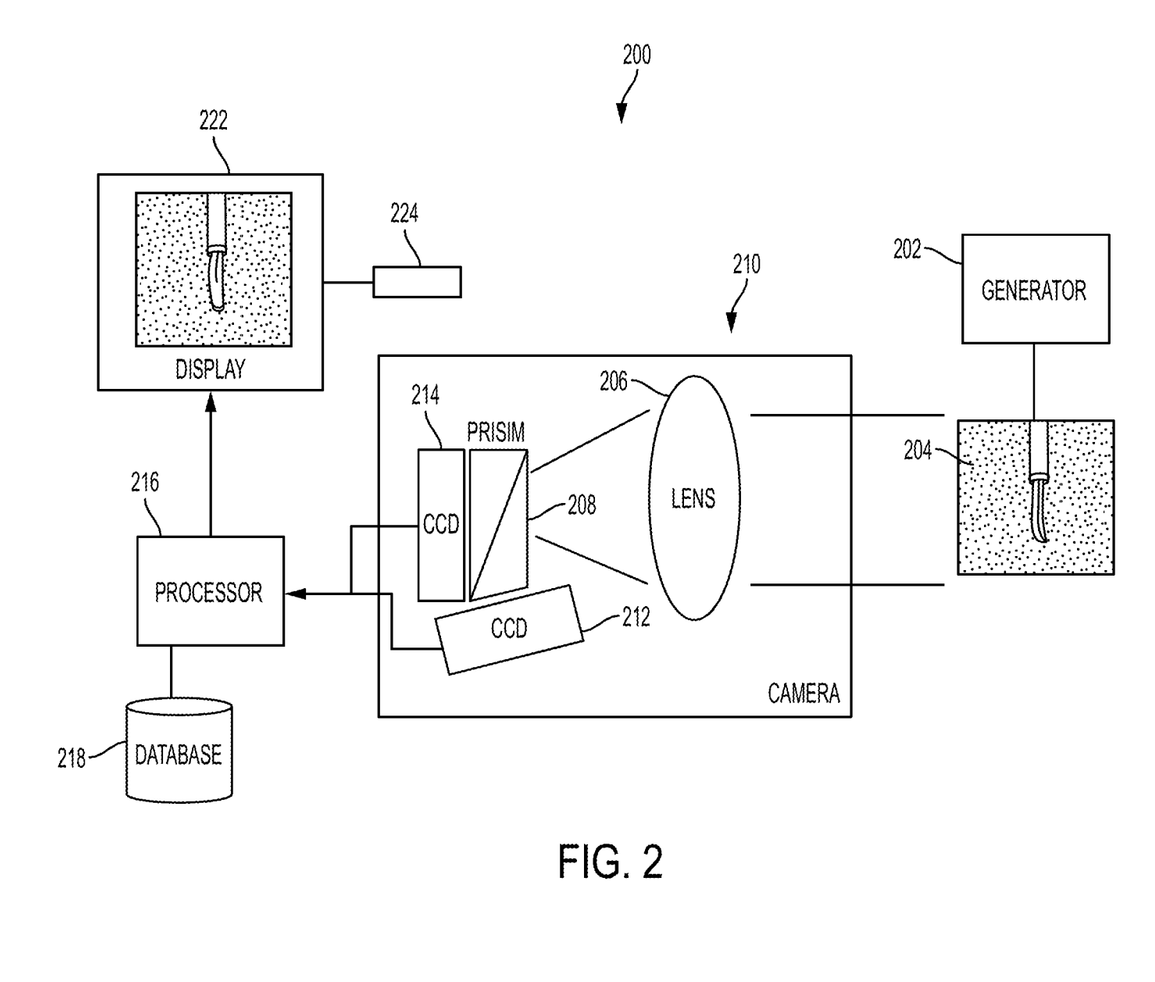
FIG. 2 illustrates a schematic view of a hot device indication system.

FIG. 2 is a schematic view of an example of surgical system 200 configured to generate modified images of a surgical site (e.g., surgical instrument 204, target tissues, tissues surrounding target tissues, etc.) in real-time. The surgical system 200 includes a camera module 210 configured to capture visible-light and infrared images of the surgical instrument 204, and relay one or more signals related to captured images to a processor 216. The signals can be relayed to the processor 216 wirelessly (Bluetooth, WiFi, etc.) or through a data cable (e.g., optical fiber, coaxial cable, etc.). The processor 216 can generate a modified image based on the captured images and information stored in the database 218. The modified image can be displayed, for example, to a surgeon, on a display 222.

A light source (not shown) can generate light which is reflected by the surgical site. A portion of the reflected visible-light (e.g., having a wavelength of about 400 nm to 800 nm) is captured by the camera module 210. The camera module 210 comprises a lens 206 configured to focus visible light and infrared radiation (collectively hereinafter referred to as "aggregate radiation") onto a first detector 212 and a second detector 214. The camera module 210 also includes an optical system 208 configured to direct a first part of the radiation to a first detector 212, and a second part of the aggregate radiation second detector 214. The quality of the visible-light and infrared image can be improved, for example, by placing detectors 212 and 214 in the focal plane of the lens 206. In one example the lens 206 is made of a material (e.g., germanium) that does not substantially absorb visible-light and infrared radiation.

The generator 202 is configured to generate a signal that drives the surgical instrument. For example, the signal may drive an ultrasonic transducer in the surgical instrument and/or generate radio frequency energy which the surgical instrument can deliver to a tissue through an energy-delivering end effector. As a result of its energy-delivering functionality, the surgical instrument typically heats up and radiates a broad spectrum of electromagnetic radiation during use. The shape of the spectrum is related to the temperature of the surgical instrument. For temperatures below about 1000° C. the electromagnetic radiation primarily includes infrared radiation. A portion of the infrared radiation generated by the surgical instrument is captured by the camera module 210. Infrared radiation can be categorized based on wavelength: near-infrared (NIR) (approximately 700-1400 nm), short-wavelength infrared (SWIR) (approximately 1400 nm-3 microns), mid-wavelength infrared (MWIR) (approximately 3-8 microns), long-wavelength infrared (LWIR) (approximately 8-15 microns), and far-infrared (FIR) (approximately 15-1000 microns).

The processor 216 receives a second signal—either directly from the surgical instrument 204 or from another device that is in communication with the surgical instrument—that includes information related to the identity of the surgical instrument, operational parameters of the surgical instrument, etc. Once the processor 216 has identified the surgical instrument, it can access various information associated with the surgical instrument 204 that may be stored in the database 218. This information may be used in generating the modified image of the surgical instrument 204, which can be displayed on a display 222. An operator can communicate with the processor 216 through an input device 224 (e.g., keyboard, mouse, joystick, etc.). For example, the operator can interact (e.g., zoom in, zoom out, mark up, etc.) with an image using the input device 224. Additionally or alternately, the operator may choose to view the visible-light/infrared image of the surgical instrument 204, operational parameters associated with the surgical instrument 204 and camera module 210, etc.

As noted above, the optical system 208 receives aggregate radiation from the surgical site, and directs a first portion of the aggregate radiation to the first detector 212, and directs a second portion of the aggregate radiation to the second detector 214. In one embodiment, the optical system 208 can be a beam splitter cube that reflects the first portion of the aggregate radiation, and transmits the second portion to the aggregate radiation. An exemplary beam splitter cube can be in the form of two triangular prisms that are joined together along their respective edges, such as by a transparent resin. The aggregate radiation travels through the first triangular prism and impinges on the transparent resin. The first portion of the aggregate radiation is reflected by the transparent resin while the second portion of the aggregate radiation is transmitted to the second triangular prism. The thickness of the transparent resin determines the ratio of the intensity between the reflected first portion and the transmitted second portion of the aggregate radiation. In other embodiments, the beam splitter can include dielectric mirrors, half-silvered mirror, etc.

Figure 3:
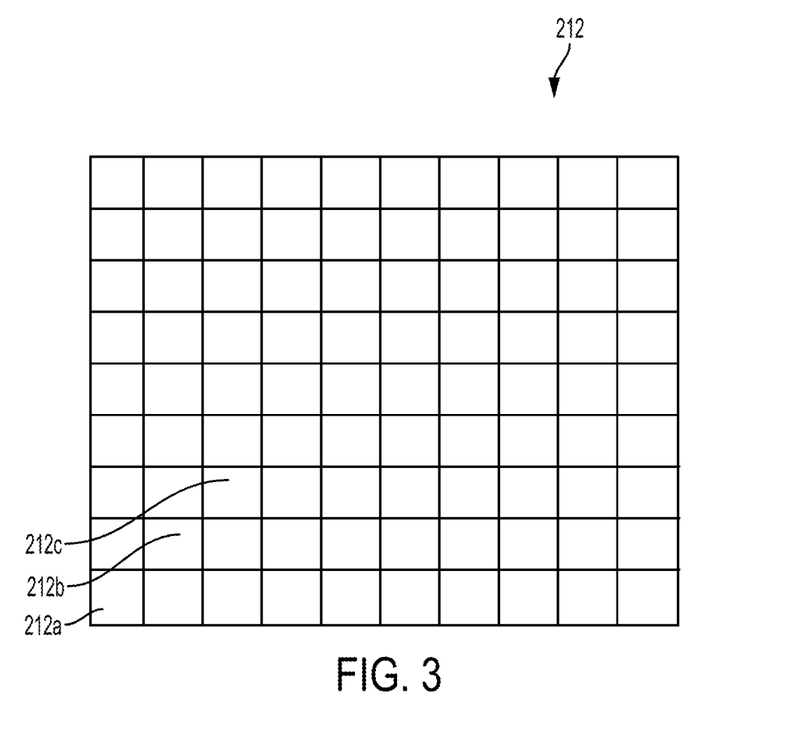
FIG. 3 illustrates a schematic view of a detector in a camera module in the surgical robotic system.

The detectors 212 and 214 are able to detect the first and second portions of the aggregate radiation, respectively. As shown in FIG. 3, an exemplary detector 212 comprises an array of photosensitive sites (e.g., 212a-c, etc.), which can absorb electromagnetic radiation impinging on the site, and generate an electrical signal (e.g., voltage signal, current signal, etc.) that is representative of the electromagnetic radiation impinging on the photosensitive site. For example, the strength of the electrical signal can be proportional to the intensity of the impinged electromagnetic radiation. Photosensitive sites typically have a spectral range which determines the range of frequencies that can be efficiently detected by the site. For example, a silicon (Si) photosensitive site can detect visible to near infrared radiation (spectral range 400-1000 nm), and a germanium (Ge) or indium gallium arsenide (InGaAs) photosensitive site can detect near infrared radiation (spectral range 800-2600 nm), and a Mercury-cadmium-telluride (HgCdTe) photosensitive site can detect light having a wavelength in the range of 800-2500 nm. It is understood that a suitable type of photosensitive site that is appropriate for the spectral range of the electromagnetic radiation to be detected can be selected.

A photosensitive site can be configured to detect a desired wavelength (or a narrow range of wavelength around the desired wavelength) of electromagnetic radiation that lies within its spectral range by using an optical filter. The optical filter, which is placed in the path of the electromagnetic radiation directed towards the photosensitive site, filters out all radiation except for that corresponding to the desired wavelength. For example, a Si photosensitive site (e.g., 212a) with an NIR filter will primarily detect radiation with near infrared wavelengths even though its spectral range includes visible-light. Alternately, if a green color filter is used, the photosensitive site will primarily detect green light (approximately 500 nm).

In one example a detector (e.g., detectors 212 and 214) detects an image of the surgical site by combining the images of different regions of the object captured by various photosensitive sites in the detector. When the first portion of the aggregate radiation impinges on the detector 212, a photosensitive site therein (e.g., 212a, 212b, 212c, etc.) detects a part of the first portion of aggregate radiation that represents an image of a region of the surgical instrument. The photosensitive site then generates an electrical signal that is representative of the captured image. This electrical signal is converted to a digital signal by an analog-to-digital converter (ADC). The digital signal has discretized values that represent, for example, the intensity of the detected radiation. As will be described below, the digital signal can also include information related to the frequency (color) of the detected radiation. The values of the digital signals from the various photosensitive sites (collectively referred to as an image dataset) are representative of the image of the surgical instrument. There can be a one-to-one relationship between a digital signal value stored in the image dataset and the photosensitive site that has produced the digital signal value (e.g., the digital signal value can include information that identifies photosensitive site that has generated the digital signal). Therefore, by identifying a digital signal value in the image dataset one can identify the photosensitive site that generated the digital value (or vice-versa). The processor then generates the image of the surgical site from the image dataset that can be displayed on a display device 222 (e.g., a monitor). Each pixel in the display device can represent one digital signal value in the image dataset. In other words, each pixel in the display device can represent the radiation detected by a unique photosensitive site in the detector 212.

A colored image of a surgical site can be generated by placing optical filters (or an array of optical filters) in the path of the electromagnetic radiation directed towards a detector. For example, an array of color filters (e.g., Bayer filter, RGBE filter, CYYM filter, CYGM filter, etc.) can be placed before an array of photosensitive sites. As a result, each photosensitive site receives electromagnetic radiation of a particular wavelength (or color). For example, for a Bayer filter, each photosensitive site detects one of red, blue or green color. The processor can use a demosaicing algorithm to process an image dataset obtained using a Bayer filter to generate a "full-color" image (i.e., an image with multiple colors).

As illustrated in FIG. 2, the optical system 208 directs a first portion of the aggregate radiation to the first detector 212, and a second portion of the aggregate radiation to the second detector 214. If a visible-light optical filter is placed before the first detector 212, it will detect a visible-light image of the surgical site. As a result, a visible-light image dataset is generated (as described above) and transmitted to the processor 216. The visible-light image dataset can include information related to the intensity and wavelength (color) of the detected visible-light for each photosensitive site. As described above, the color of the detected visible-light depends on the optical filter. If an infrared optical filter is placed before the second detector 214, it will detect an infrared image of the surgical site. Based on this detection, an infrared image dataset is generated (as described above) and transmitted to the processor 216.

The processor can identify data related to the image of surgical instrument from the visible-light image dataset. In one embodiment, the data is identified based on a predetermined relative position between the first detector 212 and the surgical instrument 204. In this embodiment, the camera module 210 is attached to the surgical instrument such that the relative position of the surgical instrument with respect to the camera module 210 remains fixed. This can be done, for example, by having a mounting feature on the surgical instrument to which the camera module 210 can be removably attached. Devices (detectors 212 and 214, prism 208, lens 206, etc.) inside the camera module 210 can be positioned in a predetermined configuration. Alternately, the devices can be attached to piezoelectric actuators that allow them to move relative to one another. This can allow the detectors (212 and 214) to detect a sharp image of the surgical instrument. For example, it can be desirable to place the detectors (212 and 214) in the focal plane of the lens 206. Mechanical movements and thermal expansion of the camera module 210 and the devices therein can move the detectors out of the focal plane of the lens. The detectors can be adjusted back into the focal plane by the piezoelectric actuators that can be controlled by the processor 216, or by an input from a user. The input from the user can be communicated to the camera module 210 using wireless short-range communication (e.g., bluetooth). The surgical instrument 204 and the camera module 210 (and the devices inside the camera module) can be adjusted to a desired predetermined position prior to the insertion of camera module 210 and surgical instrument 204 in the surgical site. The photosensitive sites (in detectors 212 and 214) that capture the image of the surgical instrument 204 can be identified based on the predetermined orientation of the detectors (e.g., 212 and 214) and the surgical instrument. Information related to the location of the aforementioned photosensitive sites can be stored in the database 218. The processor 216 can identify surgical instrument image data in the visible-light image dataset. This can be done, for example, by arranging the image data, captured by the photosensitive sites, in a predetermined pattern in the visible-light image. For example, the image data captured by the photosensitive site 212a can be placed at a predetermined location in the visible-light dataset. Information about this relationship can be stored in an index data file in the database 218. Based on the index data file, the processor 216 can identify the image data (from the visible-image dataset) corresponding to the image detected by the photosensitive site 212a. Alternately, the image data can include information that identifies the photosensitive site that generated it. Similarly, processor 216 can identify data related to the surgical instrument in the infrared image dataset.

Figure 4:
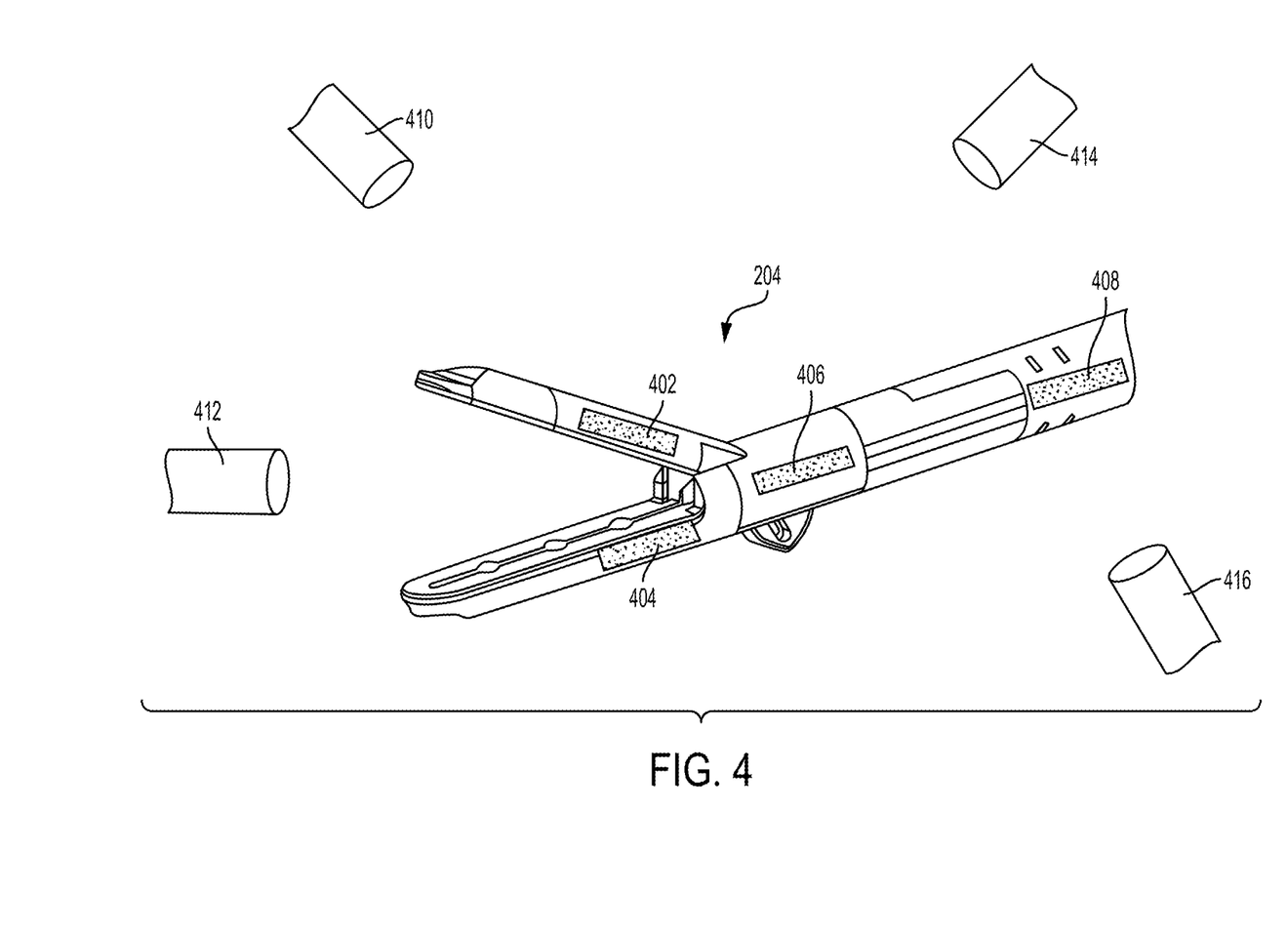
FIG. 4 illustrates a surgical instrument positioned in a field having multiple markers.

In another embodiment, the surgical instrument is identified in the visible-light image based on one or more markers on the surgical instrument 204, and multiple cameras 410, 412, 414, 416 are used to image the surgical site. As shown in FIG. 4, the surgical instrument 204 includes a number of markers 402, 404, 406, 408 located on its surface. In one embodiment the markers are regions on the surgical instrument 204 that reflect electromagnetic radiation of a given frequency. For example, the markers can be configured to reflect visible-light of a certain color. The color of the markers can be selected such that the color is not naturally present in the surgical site (e.g., green, blue, etc.). The processor thus identifies photosensitive sites that detect the image of the markers based on marker color. As described above, the visible-light image dataset can include, for each photosensitive site, information related to the color of the detected visible-light. The processor can search in the visible-light image dataset for data representative of the color of the marker. The processor 216 identifies the markers 402, 404, 406, 408 (and therefore the relative positions of the markers) in the visible-light image and compares this information with data from a database of surgical instruments stored in the database 218. The database includes information related to marker color and marker position for various surgical instruments. Additionally, for a given surgical instrument, the database may include information related to the relative position of the makers in an image of the surgical instruments from multiple viewpoints. For example, the relative positions of the markers 402, 404, 406, 408 in the image of the surgical instrument 204 in the embodiment of FIG. 4 will depend on the relative position of the camera (e.g., 410, 412, 414, 416) that captures the image.

The processor can use an image recognition algorithm to identify the data in the visible-light dataset that represents the image of the surgical instrument. In one example the image recognition algorithm receives input information related to the position of the markers in the captured image, and information related to various surgical instruments stored in the database 218. The processor compares the relative positions of markers in the captured image with the orientation information of markers of the devices in the database by using various pattern recognition techniques. Based on this comparison, the processor can identify data representative of image of the surgical instrument 204 in the visible-image dataset. It is understood that the markers may comprise a geometric shape and/or color, either as something that is applied to the device (for example green dots) or could as something that is inherent to a type of device (e.g., silver straight jaws and blacked shaft).

In this embodiment, the first detector 212 and the second detector 214 can have a predetermined relative orientation. The photosensitive sites in the second detector that capture the image of the surgical instrument can be determined based on the knowledge of the photosensitive sites in the first detector that capture the image of the surgical instrument. Once the photosensitive sites in the second detector 214 that capture the image of the surgical instrument are identified, the processor 216 can identify data related to surgical instrument image in the infrared image dataset.

The processor is configured to calculate the temperature of various regions of the surgical instrument based on the captured infrared image. The temperature of an object is related to the amount of infrared radiation emitted by the object. An object at a given temperature emits a spectrum of electromagnetic radiation (referred to as black-body radiation). For example, the surgical instrument 204 at an operational temperature (e.g. 50° C.) emits a spectrum of infrared radiation. The frequency of the infrared spectrum is related to the temperature of an object by an emissivity parameter, which is inherent to the material(s) from which the surgical instrument is made. The known emissivity parameter values for a given surgical instrument, and information related to the location of the corresponding regions on the surgical instrument, are stored in the database 218. The processor 216 is thus able to calculate the temperature of a region on the surgical instrument based on the amount of detected infrared radiation from the region and the emissivity parameter associated with the region. The intensity of the radiation is then converted into an electrical signal. That is, as more radiation excites the sensor to a greater extent, the processor equates the greater electrical signal received from the sensor into a higher temperature.

The processor 216 can assign colors to the various regions of the surgical device based on the detected temperature of the region. For example, the processor can assign a red color to the regions of the surgical device that are at or above 50° C., and another color (e.g., white or green) is assigned to regions of the surgical device that are below 50° C. The processor can generate a modified image of the surgical instrument in which the assigned colors are superimposed on visible-light image of the surgical device. For example, in the modified image, which can be displayed on the display 222, the regions of the surgical instrument that are at or above a predetermined temperature are highlighted with a predetermined color (e.g., red). It is understood that in addition to or as an alternative to the use of colors to denote temperature, other symbols or indicia can be used. For example, icons or shapes (e.g., "stars", "*", "+", or "!".) may be overlaid on the image. In addition, or alternatively, brightness may be increased to near white, or dynamic color shifting or animation of pixels (e.g., pulsing between natural color and alternate color.) may be utilized.

Figure 5:
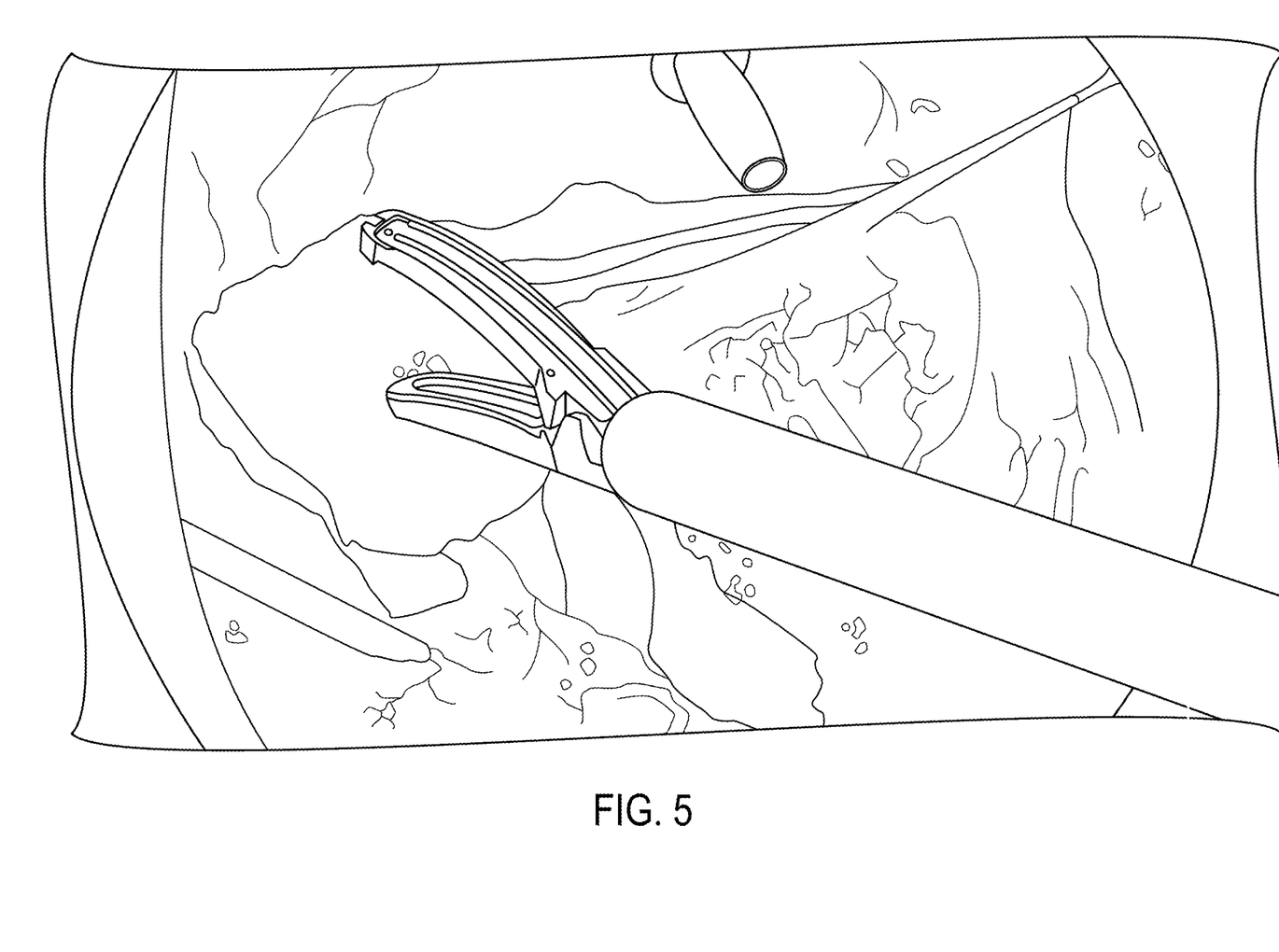
FIG. 5 illustrates a modified image of the surgical instrument that highlights regions of the surgical instrument above a predetermined temperature.

FIG. 5 illustrates a modified image of an advanced bipolar vessel sealer device in a surgical site. In this depiction the jaws of the endocutter are above 50° C. and thus include indicia (i.e., highlighting) to indicate to the surgeon that the jaws are at or above a threshold temperature. As a result, a surgeon viewing the modified image in real time during a surgical procedure is immediately aware of the regions of the surgical instrument that are at or above the threshold temperature and potentially able to damage tissue.

Figure 6:
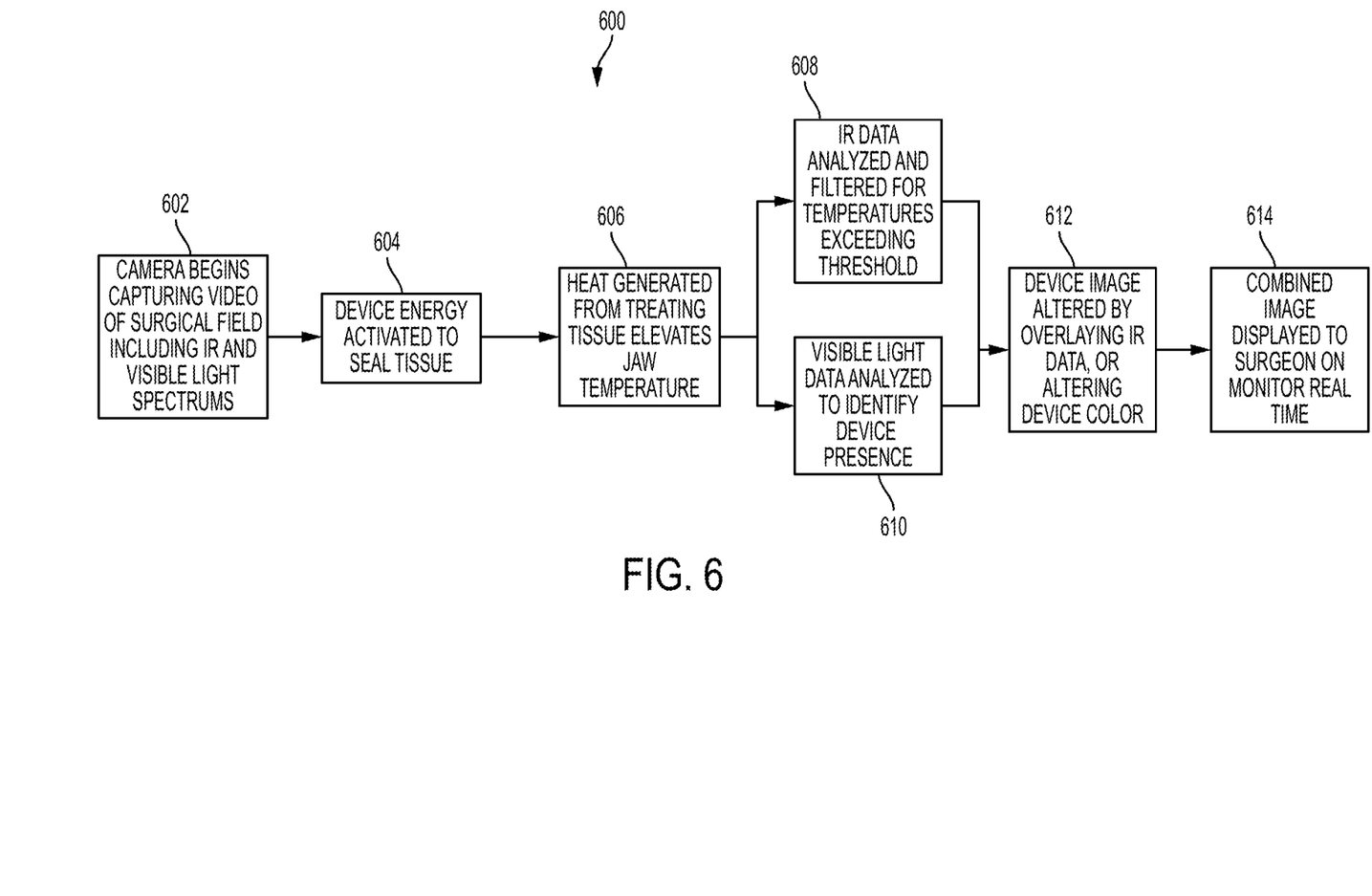
FIG. 6 illustrates a flowchart describing a method of creating a modified image of a surgical instrument to indicate the instrument's status.

FIG. 6 illustrates a flowchart depicting a method of creating a modified image of a surgical instrument to indicate the instrument's status (e.g., temperature). The camera module begins capturing a series of images (step 602) of the surgical site (for example, a video). These images include both visible-light images and infrared images. The generator 202 activates the surgical instrument (step 604) and the end effector of the surgical device heats up and emits infrared radiation (step 606). The processor 216 analyzes the captured infrared image to detect regions of the surgical instrument that are at or above the predetermined threshold temperature (step 608). At the same time, the processor 216 analyzes the captured visible-light image to identify the image of the surgical device (step 610). The processor 216 then generates a modified image of the surgical instrument by altering the visible-light image (step 612). For example, regions of the surgical instrument above the threshold temperature include indicia (e.g., they are highlighted in red color) to indicate regions of the surgical device at or above the threshold temperature. The series of modified captured images are then displayed on a display device (e.g., a wall or table mounted display or a display that is part of an accessory, such as a head set, worn by a surgeon) to be monitored by the surgeon (step 614).

Figure 7:
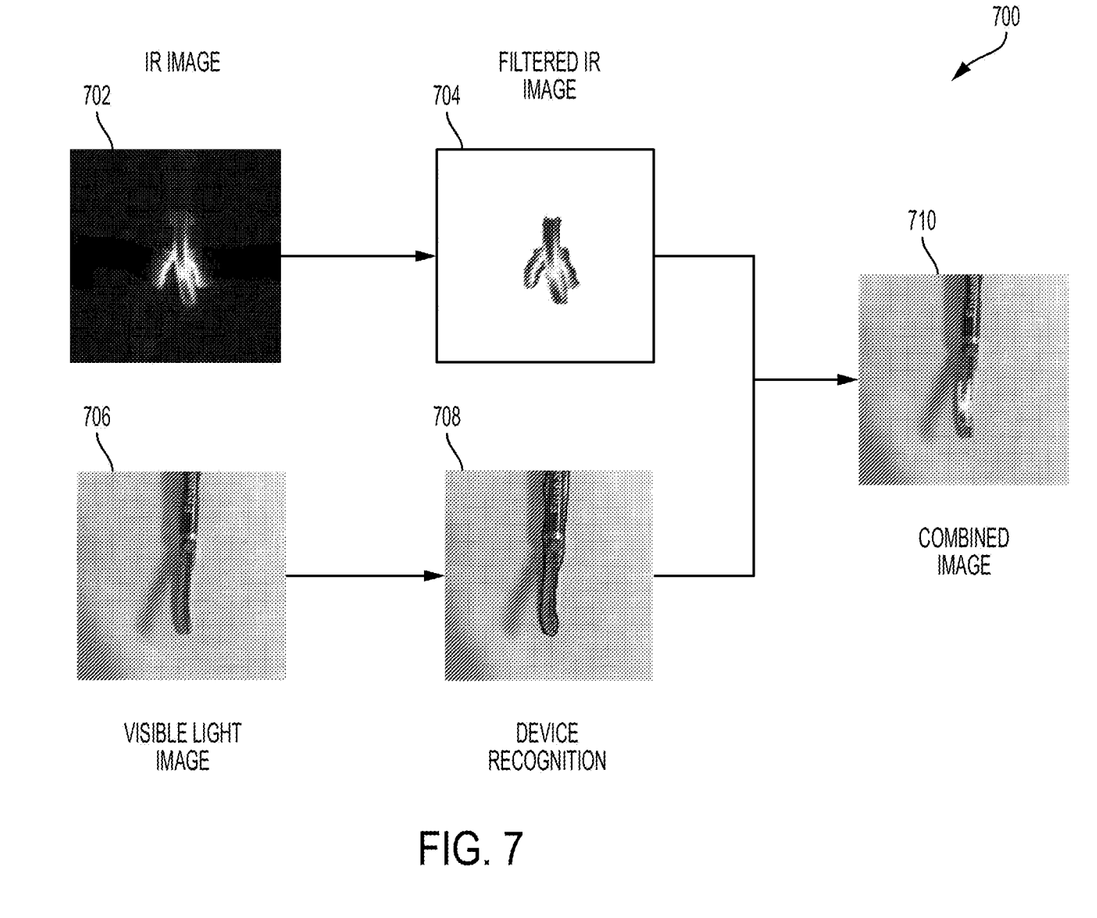
FIG. 7 illustrates the visual image, the infrared image and the superimposed image described in FIG. 6.

FIG. 7 schematically illustrates examples of the infrared image 702 and the visible-light image 706 of the surgical instrument captured by the camera module 210. The processor identifies the surgical instrument from the visible-light image 706 and generates a filtered infrared image 704. The processor then generates a modified image 710, which is a superposition of the filtered infrared image 704 and the visible-light image 706.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to a user and a keyboard and a pointing device, e.g., a mouse, a trackball, etc., by which a user may provide input to the computer. Other kinds of devices can be used to provide for interaction with a user as well. For example, feedback provided to a user can be any form of sensory feedback, such as for example visual feedback, auditory feedback, or tactile feedback; and input from a user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 8:
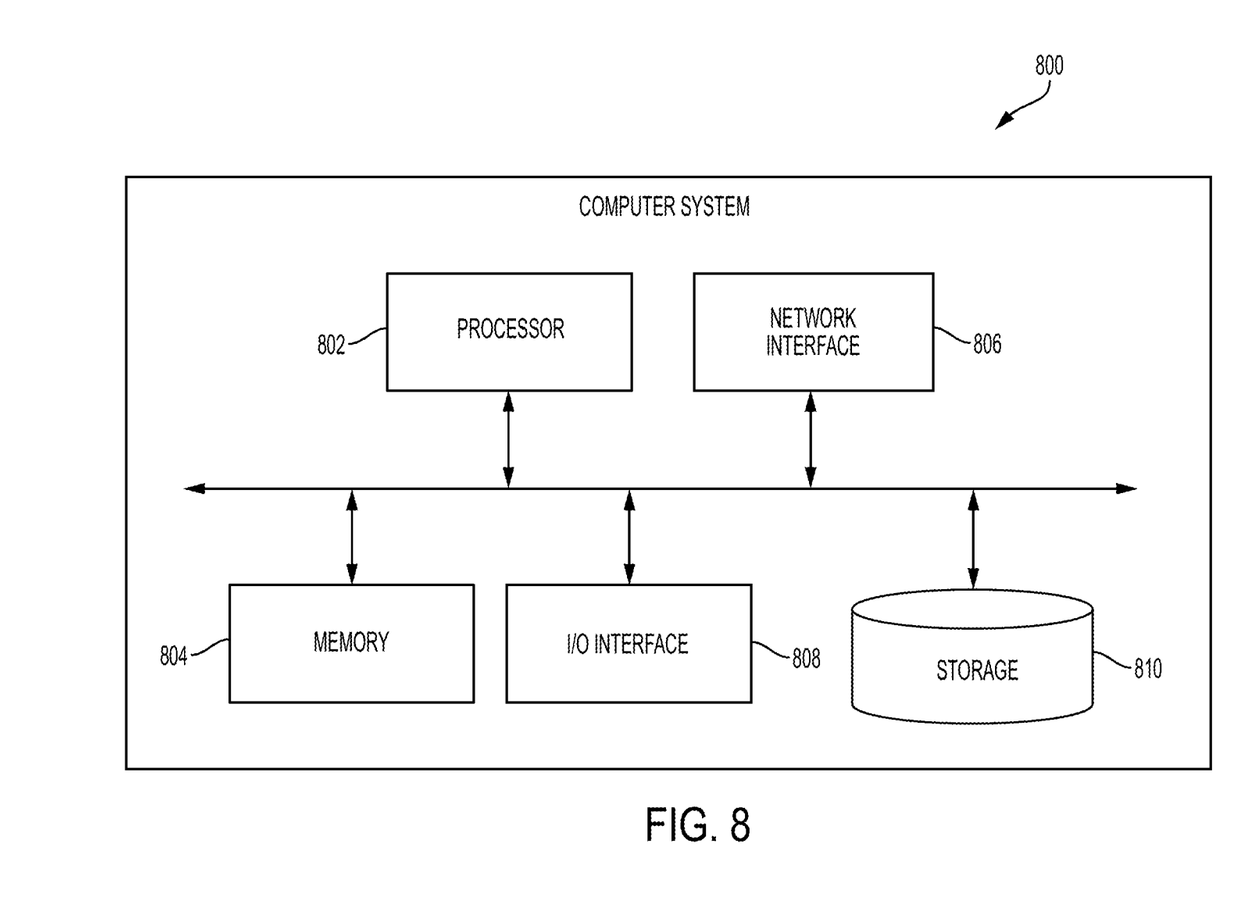
FIG. 8 is a schematic illustration of a computer system configured to generate a plurality of command signals for use with the control system described herein.

FIG. 8 illustrates an exemplary embodiment of a computer system 800. As shown, the computer system 800 includes one or more processors 802 which can control the operation of the computer system 800. "Processors" are also referred to herein as "controllers." The processor(s) 802 can include any type of microprocessor or central processing unit (CPU), including programmable general-purpose or special-purpose microprocessors and/or any one of a variety of proprietary or commercially available single or multi-processor systems. The computer system 800 can also include one or more memories 804, which can provide temporary storage for code to be executed by the processor(s) 802 or for data acquired from one or more users, storage devices, and/or databases. The memory 804 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 800 can be coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 can also include one or more network interface(s) 806, one or more input/output (IO) interface(s) 808, and one or more storage device(s) 810.

The network interface(s) 806 can enable the computer system 800 to communicate with remote devices, e.g., other computer systems, over a network, and can be, for non-limiting example, remote desktop connection interfaces, Ethernet adapters, and/or other local area network (LAN) adapters. The IO interface(s) 808 can include one or more interface components to connect the computer system 800 with other electronic equipment. For non-limiting example, the IO interface(s) 808 can include high speed data ports, such as universal serial bus (USB) ports, 1394 ports, Wi-Fi, Bluetooth, etc. Additionally, the computer system 800 can be accessible to a human user, and thus the IO interface(s) 808 can include displays, speakers, keyboards, pointing devices, and/or various other video, audio, or alphanumeric interfaces. The storage device(s) 810 can include any conventional medium for storing data in a non-volatile and/or non-transient manner. The storage device(s) 810 can thus hold data and/or instructions in a persistent state, i.e., the value(s) are retained despite interruption of power to the computer system 800. The storage device(s) 810 can include one or more hard disk drives, flash drives, USB drives, optical drives, various media cards, diskettes, compact discs, and/or any combination thereof and can be directly connected to the computer system 800 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 8 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

In an exemplary embodiment, the computer system 800 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system comprising:
a first detector, comprising a first array of pixels configured to detect light reflected by a surgical instrument and generate a first signal comprising a first dataset representative of a visible image of the surgical instrument;
a second detector, comprising a second array of pixels configured to detect infrared radiation produced by the surgical instrument during a procedure using the surgical instrument and generate a second signal comprising a second dataset representative of an infrared image of the surgical instrument;
an optical system configured to direct at least a portion of the light reflected by the surgical instrument to the first detector and direct at least a portion of the infrared radiation produced by the surgical instrument to the second detector; and
a processor configured to:
receive the first and second signals,
identify from the first dataset data representative of the surgical instrument,
identify from the second dataset data representative of one or more regions of the surgical instrument above a predetermined threshold temperature, and
generate a modified image of the surgical instrument based on data identified from the first and second dataset, the modified image including visible indicia in the one or more regions of the surgical instrument at or above the predetermined temperature and the modified image configured to be displayed in a display screen.

2. The system of claim 1, comprising a lens to direct the visible light reflected by the surgical instrument and the infrared radiation produced by the surgical instrument to the optical element.

3. The system of claim 1, wherein the processor is configured to identify data representative of the surgical instrument based on position of the first detector with respect to the surgical instrument.

4. The system of claim 3, wherein the processor is configured to determine orientation of the surgical instrument based on the identified data representative of the surgical instrument and a database of one or more surgical instruments stored in memory.

5. The system of claim 1, wherein the surgical instrument includes one or more markers, each of the one or more markers configured to reflect a predetermined frequency of light.

6. The system of claim 1, wherein the processor is configured to identify from the second dataset data representative of one or more regions of the surgical instrument above the predetermined threshold temperature based on the frequency of the infrared radiation produced by the one or more regions of the surgical instrument.

7. The system of claim 1, wherein the surgical instrument comprises an energy delivering end effector configured to deliver at least one of ultrasonic energy and radio frequency energy to a tissue.

8. The system of claim 1, further comprising a display device to display the modified image.

9. The system of claim 1, wherein the surgical system is a robotic surgical system and the robotic surgical system comprises at least one robotic arm configured to hold and manipulate the surgical instrument.

10. The system of claim 1, wherein the predetermined threshold temperature is 50° C.

11. The system of claim 1, wherein the visible indicia comprises pixels of a distinct color in the modified image that represent a temperature value at or above the predetermined threshold temperature.

12. The system of claim 11, wherein the color is red.

* * * * *